United States Patent [19]

Reichert et al.

[11] Patent Number: 5,490,500

[45] Date of Patent: Feb. 13, 1996

[54] ANESTHETIC EVAPORATOR WITH INTERMEDIATE CONTAINER

[75] Inventors: Dirk-Stefan Reichert; Günther Hahmann, both of Lübeck; Wolfgang Falb, Krummesse, all of Germany

[73] Assignee: Drägerwerk AG, Lubeck, Germany

[21] Appl. No.: 255,653

[22] Filed: Jun. 8, 1994

[30] Foreign Application Priority Data

Jun. 24, 1993 [DE] Germany .................... 43 20 921.1

[51] Int. Cl.$^6$ ................................... A61M 16/00
[52] U.S. Cl. ............................ 128/204.13; 128/203.12; 128/200.21
[58] Field of Search .................. 128/203.16, 203.17, 128/204.13, 203.26, 203.27, 203.12, 203.25, 200.21

[56] References Cited

U.S. PATENT DOCUMENTS

| | | | |
|---|---|---|---|
| 3,651,805 | 3/1972 | Bneiling | 128/203.25 |
| 4,017,566 | 4/1977 | Seidel | 261/56 |
| 4,067,935 | 1/1978 | Jones et al. | 128/203.14 |
| 4,444,182 | 4/1984 | Gregory | 128/204.14 |
| 4,693,853 | 9/1987 | Falb et al. | 128/204.13 |
| 4,879,997 | 11/1989 | Bieleford | 128/200.21 |

Primary Examiner—Edgar S. Burr
Assistant Examiner—V. Srivastava
Attorney, Agent, or Firm—McGlew and Tuttle

[57] ABSTRACT

An anesthetic evaporator according to the bypass principle, in which a carrier gas system is partially led through an evaporation chamber, is enriched with an anesthetic vapor to saturation there, and is again fed into the bypass flow. The function of the elements that influence the metering are not impaired by the penetration of anesthetic in an unintentional position other than the position intended for operation, and that the anesthetic located in the mixed gas outlet is not influenced by anesthetic located outside the evaporation chamber. Either the evaporation chamber line leading to the evaporation chamber or the return line leading from the evaporation chamber to the flow regulating valve opens into an intermediate container, from which a channel communicates with the interior of the evaporation chamber. Anesthetic once penetrated into the intermediate container cannot accumulate even when the anesthetic evaporator is repeatedly placed into an unintended position, but an amount which does not impair the function of the anesthetic evaporator will remain in it [the intermediate container], or it evaporates during the operation, or it can again be emptied into the evaporation chamber in a simple manner.

16 Claims, 7 Drawing Sheets

ANESTHETIC EVAPORATOR WITH INTERMEDIATE CONTAINER

FIELD OF THE INVVENTION

The present invention pertains to an anesthetic evaporator according to the bypass principle, in which an evaporation chamber containing the liquid anesthetic with a wick device impregnated with anesthetic is provided, into which a carrier gas flow, originating from a gas inlet and led via an evaporation chamber line, opens, which carrier gas flow unites via a return line with the carrier gas flowing in a bypass line after becoming enriched with evaporated anestheic, which bypass line forms a connection bypassing the evaporatinn chamber between the gas inlet and a mLxed gas outlet, wherein a flow regulating valve, which is adjustable via an adjusting device, is arranged in the course of the return line to meter the carrier gas enriched with anesthetic into the bypass line.

BACKGROUND OF THE INVENTION

Anesthetic evaporators are used in conjunction with anesthesia apparatuses in order to enrich a carrier gas, usually a laughing gas-oxygen mixture or an air-oxygen mixture, with a volatile anesthetic. The anesthetic is filled in the liquid state into the evaporation chamber, which is equipped with a wick device, which is completely soaked with the anesthetic and releases the evaporating liquid anesthetic from its surface to the carrier gas flowing through the evaporation chamber. The wick device may be, e.g., a wick made of nonwoven felt or another nonwoven-like knit material, but it may also consist of a porous, absorbent body, e.g., sintered glass, which is in liquid contact with the anesthetic. The percentage of gaseous anesthetic in the carrier gas is usually a few volume percent. To set this percentage, and also to change it during the anesthesia as needed, a metering unit, which is adjustable via a handwheel, is located on the anesthetic evaporator. The majority of the carrier gas flow flows past the evaporation chamber in a bypass line. A small percentage of the carrier gas is led from a branch of the carrier gas into txe evaporation chamber, in which it is enriched with the anesthetic to saturation and is fed via an adjustable metering gap into the rest of the carrier gas flow in the bypass line A mixed gas, which contains a percentage of gaseous anesthetic adjustable by means of the metering unit, is thus obtained. The percentage of anesthetic in the mixed gas is changed by changing the width of the metering gap. The gaseous anesthetic of such a composition is led from a mixed gas outlet to an anesthesia apparatus, by which the gaseous anesthetic is fed to the patient to be treated.

Such an anesthetic evaporator is described in DE-25,07,261 A1 (U.S. Pat. No. 4,017,566). In this evaporator the anesthetic is contained as a filling in a pot-like evaporation chamber in the evaporator, and the impregnated wicks immerse into the liquid reserve.

Part of the carrier gas flows via an evaporation chamber line into the interior of the evaporation chamber, is enriched with the anesthetic gas at the wicks, leaves the evaporation chamber via a return line, and flows through the metering gap into the bypass line. The anesthetic gas is mixed there with the rest of the carrier gas and is led as a mixed gas to the mixed gas outlet. The evaporation of the anesthetic brings about a change in temperature in the area of the evaporation chamber (latent heat) as a function of the carrier gas flow, depending on the setting of the concentration by changing the width of the metering gap. If the setting of the metering gap, once set, which acts as a flow regulating valve, were left unchanged, the anesthetic concentration in the mixed gas would therefore change; it is reduced by cooling. The change in the ambient temperature also affects the metering. It is therefore also necessary to change the metering gap acting as a flow regulating valve, once set, depending on the change in temperature. A temperature compensation device, which changes the gap width and consequently the flow resistance of a flow regulating valve in the bypass line via a temperature-dependent change, is therefore provided in the prior-art anesthetic evaporator.

Since the liquid anesthetic reserve is stored in a reservoir of the evaporation chamber, it is necessary to operate the anesthetic evaporator in a certain preferred position in order to prevent liquid anesthetic from entering the flow channels, especially the flow regulating valves. The narrow metering gaps of the flow regulating valves and the lines in the bypass channel could retain liquid as a consequence of capillary forces, so that correct metering would no longer be possible. In addition, the lines carrying the carrier gas would be wetted with anesthetic, so that a concentration, once set, would not be maintained, because additional anesthetic would evaporate from the gascarrying lines in an uncontrollable manner, and it would be fed to the mixed gas outlet. While the position in the operating state of the anesthetic evaporator in the upright position can be ensured by technical means, e.g., by suitable measures on the anesthesia apparatus, oblique positions of the anesthetic evaporator may occur during the transportation of the anesthetic evaporator or even of the complete anesthesia apparatus (especially in the case of small, portable anesthesia apparatuses), or the anesthetic liquid may penetrate into gas-carrying lines, especially into the flow regulating valves, due to shaking during transportation. The possibility that the anesthetic evaporator will be in such an oblique position, in which liquid anesthetic will fill the gas-carrying flow channels in an undesired manner, also cannot be ruled out during the storage of a filled anesthetic evaporator, namely, especially during transportation from and to the place of storage. This circumstance is all the more significant as it is impossible to determine from an anesthetic evaporator standing upright in what position (lying, upright, or upside down) it has been since it was filled with anesthetic. To eliminate disadvantageous consequence of an undesired oblique position, it would be necessary to specify that the gas-carrying lines be rinsed, before an anesthetic evaporator is put into operation, until the concentration set on the handwheel is reached at the mixed gas outlet. This would lead to a delay in the putting into operation of an anesthetic evaporator, which could not be acceptable for the user, and it would require the presence of a measuring instrument. In addition, gas and anesthetic would be lost during rinsing.

U.S. Pat. No. 4,444,182 made a suggestion for avoiding the disadvantageous consequences of the oblique position of the anesthetic evaporator, and especially those of the upside down position of the anesthetic evaporatdr, in which the anesthetic reserve is no longer at the bottom, but flows at the level of the gas inlet. In this prior-art anesthetic evaporator, a plurality of gas-carrying channels, which immerse into the anesthetic liquid and are closed by it, are provided in the standard operating position, i.e., when the evaporation chamber forms the bottom of the anesthetic evaporator. If the anesthetic evaporator is tilted, or even turned upside down, the openings of one or all of the channels are exposed, so that the gas can flow via these exposed channels.

SUMMARY AND OBJECTS OF THE INVENTION

Thus, the basic object of the present invention is to improve an anesthetic evaporator of the class described such that when it is unintentionally in a position other than the position intended, the function of the elements which influence the metering in the bypass line and/or in the return line is not impaired by penetrating anesthetic, and no anesthetic outside the evaporation chamber will influence the percentage of anesthetic located in the mixed gas outlet.

This object is attained by either the evaporation chamber line and/or the return line opening into an intermediate container, which is accommodated as an independent vessel within the evaporation chamber, and by it the intermediate container having a channel, which communicates with the interior of the evaporation chamber and via which anesthetic that has penetrated can be emptied from the intermediate container.

The advantage of the present invention is essentially the fact that the carrier gas flow branched off in the evaporation chamber is first taken up in an-intermediate container, from which the carder gas flow enters the evaporation chamber to become enriched with anesthetic gas. The evaporation chamber line is led into the intermediate container in this case.

On the other hand, the carrier gas flow enriched with anesthetic in the evaporation chamber can be led through the flow regulating valve to set the anesthetic concentration only when it had passed through the intermediate container before. The return line is connected to the intermediate container in this case. Provisions may also be made to cause both the evaporation chamber line and the return line to open into a respective separate intermediate container. Thus, one of the two lines, namely, the evaporation chamber line or the return line, or even both lines, thus have a kind of anesthetic trap in the form of the intermediate container, in which anesthetic, which could otherwise flow into the evaporation chamber line or into the return line due to an unintentional oblique position or upside down position of the anesthetic evaporator, is collected, and it is prevented from penetrating into the gas-carrying lines or even into the flow regulating valve for setting the anesthetic concentration or into the flow regulating valve in the bypass channel. Should anesthetic ever have penetrated into the intermediate container, the anesthetic remains stored in it until it evaporates from the intermediate container during the standard operation of the anesthetic evaporator as a consequence of the flowing carrier gas. The intermediate container is always arranged upstream of the flow regulating valve, so that this anesthetic, which may evaporate in the intermediate container, is also taken into account by the setting of the flow regulating valve and the temperature compensation. A subsequent distortion of the anesthetic concentration, once set, due to unintentionally evaporating anesthetic in the gas-carrying lines, is not possible. Should liquid anesthetic have penetrated into the intermediate container, the intermediate container can again be emptied via the channel by intentional tilting or pivoting movements.

To limit the amount of liquid anesthetic having possibly penetrated into the intermediate container, it is advantageous to cause the channel to extend essentially in parallel to the liquid level of the anesthetic located in the evaporation chamber when the completely filled evaporation chamber is in its essentially upright operating position. On the one hand, the opening of the channel is at a spaced location from the liquid level, and, on the other hand, it is arranged, to the extent possible, centrally in relation to the wick. Thus, it extends essentially in the middle area of the evaporation chamber. This makes it possible for the opening of the channel to reach above the level of the liquic anesthetic in all oblique positions, up to and including the upside down position, without the flow of the carrier gas being hindered, and without liquid being able to penetrate into the gas-carrying lines. Unaffected evaboration of the anesthetic from the walls of the wick into the evaporation chamber is also still possible, so that the anesthetic evaporator can be operated without impairment even in its oblique position. It shall be pointed out in this connection that the anesthetic evaporation chamber according to the present invention also possesses the advantages that when no wick for increasing the evaporation surface is provided, the evaporation takes place only from the liquid surface. The present invention is also independent from the composition and/or the design of a wick.

If the intermediate container is in the middle area of the evaporation chamber, it is sufficient to provide the opening of the channel in a suitable position on the intermediate container itself. For cases in which the intermediate container is arranged in the edge area of the evaporation chamber, it is useful to cause the channel to extend in parallel to the liquid level of the anesthetic over a certain section after leaving the intermediate container, namely, in the direction of the middle area of the evaporation chamber. It is thus ensured that the channel still emerges from the liquid in a tilted position, in which the anesthetic surrounds the intermediate container.

The amount of anesthetic collected in the intermediate container is retained Ietter and it is more effectively prevented from penetrating into the evaporation chamber line or into the return line if the evaporation chamber line or the return line continues in the intermediate container with a certain depih of penetration, and the channel leaves the intermediate container in the immediate vicinity of the evaporation chamber line or the return line. The evaporation chamber line or the return line now penetrates into the intermediate container to such an extent that the opening of the evaporation chamber line or the return line extends above the liquid level becoming established in the intermediate container, and the amount of anesthetic trapped can flow back unhindered from the adjacent channel into the evaporation chamber even when the evaporation chamber is in a position in which the liquid anesthetic having penetrated into the intermediate container surrounds the evaporation chamber line or the return line.

To improve the position of the channel in relation to its alignment points (liquid surface, wick, middle area of the evaporation chamber), it is favorable to cause the channel to extend, over at least a section, in parallel to the evaporation chamber line or the return line.

It cannot be completely ruled out that despite all this, a certain amount of anesthetics will penetrate into the intermediate container through the channel under the most unfavorable conditions. To prevent the size of the intermediate container, which is necessary for this, from becoming too large, and to ensure the release of the opening of the evaporation chamber line or of the return line in the intermediate container, it is favorable to select the capacity of the intermediate container to be approximately three times the volume of the space surrounded by the channel. The amount of liquid anesthetic that could penetrate into the channel thus finds sufficient space to spread into the intermediate container, so that the risk of an unintended penetration of liquid anesthetic into the evaporation chamber line or the return line is effectively prevented from occurring.

Due to the fact that the evaporation chamber line or the return line is continued with a certain depth of penetration as a pipe into the intermediate container, the geometric shape and the volume of the intermediate container can be coordinated with one another via the depth of penetration such that the anesthetic having penetrated into the intermediate container through the channel will leave the opening of the evaporation chamber line and of the return line uncovered in both the upright operating position and a position inclined by 45° in relation to the vertical direction, in the upside down position, and in the horizontal position of the evaporation chamber. As a result, not only is liquid anesthetic prevented from penetrating into the evaporation chamber line or into the return line from the intermediate container, but it is even possible to use the anesthetic evaporator in the abovementioned extreme positions, in deviation from its upright operating position, without any significant restrictions. Neither the unhindered flow through the evaporatibn chamber, nor the wetting of the wick is jeopardized.

In a particularly simple form of the intermediate container, the intermediate container has an essentially cylindrical shape, the evaporation chamber line or the return line penetrates axially into one of its front walls, and the channel exits the intermediate container, extending flush with the front surface, adjacent to the evaporation chamber line or the return line.

To make the undesired penetration of liquid anesthetic into the intermediate container even more difficult, provisions are made for the channel having an end piece that is bent off approximately at right angles from the line section extending in parallel to the liquid level of the anesthetic. This end piece may be bent off pointing away from the anesthetic liquid level or pointing toward the anesthetic liquid level, depending on the position of the channel. The direction of the bend depends on whether the line section extending in parallel to the anesthetic liquid level is at a short distance from the liquid level (in which case the bend points away from the liquid level), or whether the line section extending in parallel to the anesthetic liquid level is located at a great distance, i.e., as far away from the liquid level as possible (in which the bend points toward the liquid level).

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF FIG. 1

Figure 1:
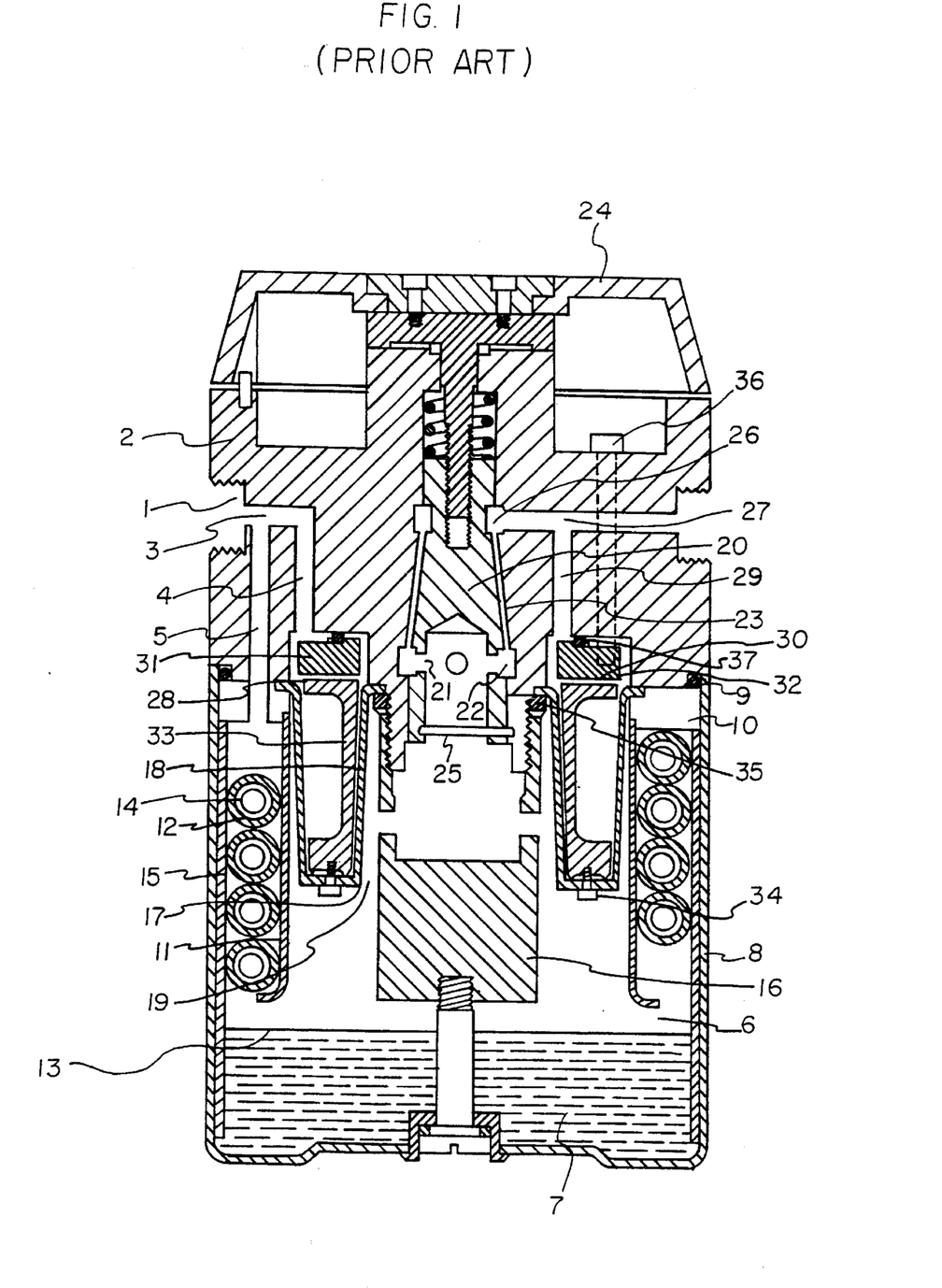
FIG. 1 is a sectional view through a prior-art anesthetic evaporator according to the state of the art.

A prior-art anesthetic evaporator is represented on the basis of FIG. 1, as it is described in the state of the art according to U.S. Pat. No. 4,071,566 corresponding to DE-25,07,261. The same reference numerals as in FIG. 1 are used for identical elements in the following FIGS. 2 through 7. Flowever, the elements are taken over from FIG. 1 only schematically.

In the prior-at anesthetic evaporator, the carrier gas fed in enters the housing 2 through the gas inlet 1. It is divided at the point of separation 3 into the bypass flow flowing through the bypass line 4 and into the evaporation chamber flow, which is led through an evaporation chamber line 5. An evaporation chamber 6 contains the liquid anesthetic 7. It is formed by a pot 8, which is gas-tightly,connected to the housing 2 via a seal 9. The seal 9 is held by a ring 10. It carries a cylinder jacket 11 on its inside. The cylinder jacket 11 has a length that ensures that the gas outlet of the evaporation chamber flow flowing from the evaporation chamber line 5 via a wick 12 above the anesthetic liquid level 13 is guaranteed. The evaporation chamber flow is guided on ihe inside and the outside along the helically wound, hose-like wick 12, which is supported by a coil spring 14 in the inward direction. The wick 12 is in connection with the wick jacket 15, which is partially immersed into the anesthetic 7 and supplies the wick 12 with anesthetic by capillary action. The evaporation chamber flow, which is saturated with anesthetic vapor in the evaporation chamber 6, flows into a metering cone 20, past a gas-guiding body 16 through a passage 19 formed by the wall 17 of a hollow ring body 18 with the gas-guiding body 16, which passage 19 acts as a return line. In the metering cone 20, it is introduced into an annular channel 22 through holes 21. The cone ring gap 23 is formed by the housing 2 and the metering cone 20. Its cross section is adjustable by means of a handwheel 24, and thus it forms the adjustable flow regulating valve 23. A pin 25 is used to prevent the metering cone 20 from co-rotating during a rotation of the handwheel 24. The evaporation chamber flow flows through the cone ring gap 23 into an annular chamber 26 and again meets the bypass flow at the junction 27. The bypass flow flows through the bypass line 4 to an annular gap 28 and through a hole 29 to the junction 27. From there, the mixed gas, enriched with anesthetic, flows to a mixed gas outlet 100, which is provided with a threaded connection, to which a mixed gas line (not shown) leading to an anesthesia apparatus, likewise not shown, can be connected. The annular gap 28 is formed by a flat surface 30 of a ring body 31 and a flat surface 32 of a hollow cylinder 33 arranged in the hollow ring body 18. The hollow cylinder 33 has a lower coefficient of thermal expansion than the hollow ring body 18. The two parts are sealingly connected to one another by screws 34. The hollow ring body 18 is held by the ring 10 on the outside and by a threaded ring 35 on the inside. In the case of changes in temperature in the evaporation chamber 6, the different coefficients of thermal expansion of the hollow ring body 18 and of the hollow cylinder 33 cause a displacement of the flat surface 32, by which the height of the annular gap 28 is changed. The ring body 31 is held on the housing 2 by screw bolts 36 via a seal 37. The screw bolts 36 are made of a material whose coefficient of thermal expansion is lower than that of the housing 2, so that the height of the annular gap changes due to the different expansion as a function of the temperature in the evaporation chamber flow. In addition, the height of the annular gap 28 and consequently the free cross section can be changed by adjusting the screw bolts 36 for adjustment via the ring body 31.

DETAILED DESCRIPTION OF THE PREFERRED EMBODIMENTS

Figure 2:
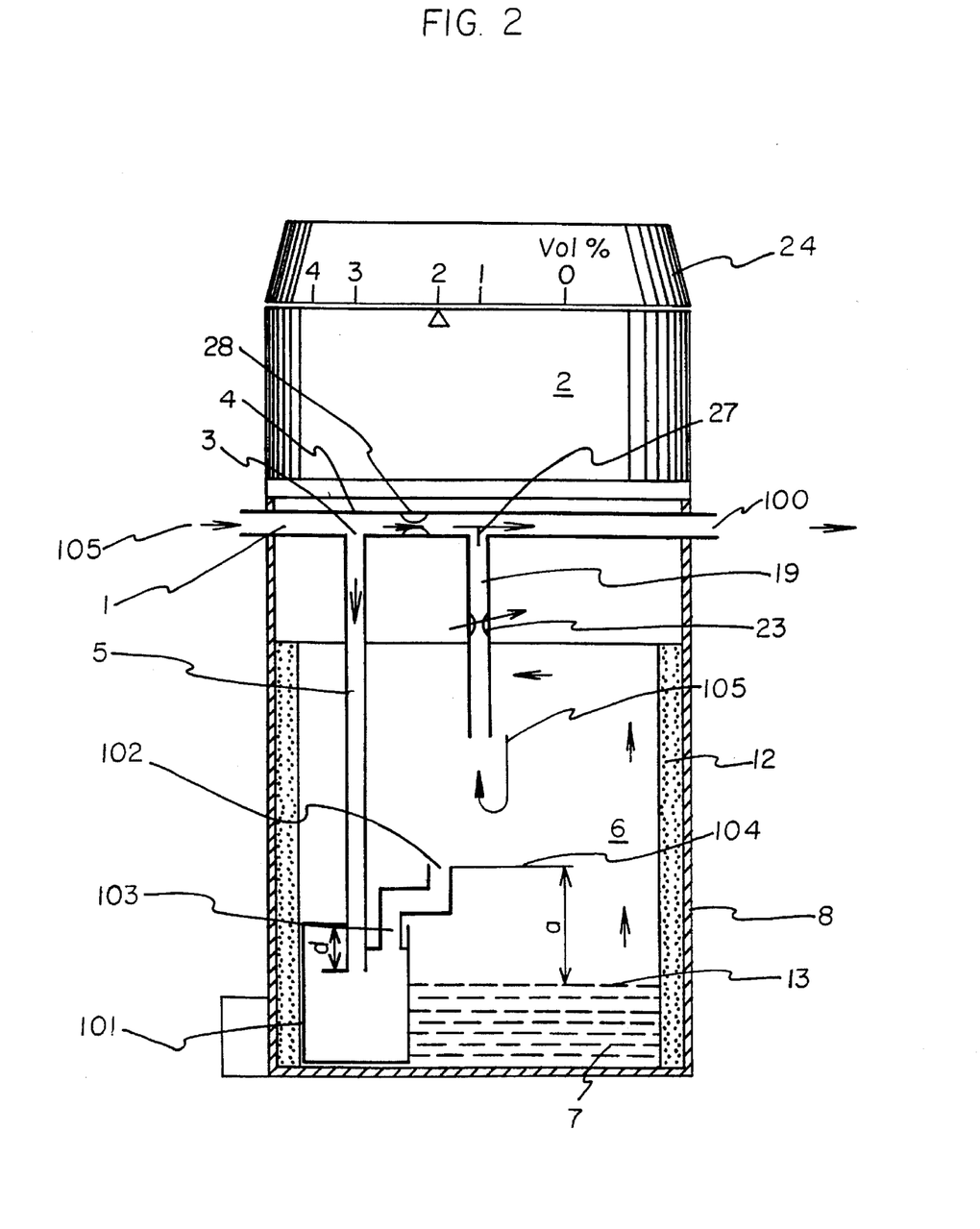
FIG. 2 is a sectional view of an anesthetic evaporator according to the present invention with an intermediate container.

The embodiment according to the present invention of the anesthetic evaporator represented in FIG. 2 opens with its evaporation chamber line 5 into an intermediate container 101, and the evaporation chamber line 5 is continued into the interior of the intermediate container 101 by a depth of penetration (d). A channel 102 is connected to the intermediate container 101 directly adjacent to the evaporation chamber line 5, and the channel 102 initially extends partially in parallel to the evaporation chamber line 5, after which it is bent at right angles, so that a line section 103 parallel to the liquid anesthetic level 13 is obtained. The line section 103 continues in a bent end piece 104, which faces away from the liquid level 13. The flow of the carrier gas and of the mixed gas enriched with the anesthetic 7 is represented by flow arrows 105. The opening of the channel 102 is located at a distance (a) from the liquid level 13 of the anesthetic 7.

The carrier gas enters the bypass line 4 via a gas inlet 1, flows past the point of separation 3 and the junction 27 and to the mixed gas outlet 100. Part of the carrier gas flow is branched off from the point of separation 3 into the evaporation chamber line 5, and ends in the intermediate container 101. The carrier gas flows into the evaporation chamber 6 from the intermediate container 101 via the channel 102. Due to appropriate guiding along the wick 12, and after sufficient swirling, it is saturated there in the evaporation chamber 6 with the liquid anesthetic 7 evaporated from the wick 12, and enters the return line 19. The passage of the return line 19 can be varied via the flow regulating valve 23 by increasing or decreasing the opening cross section of the regulating valve 23 by correspondingly adjusting the handwheel 24. The cross section set determines the division between the carrier gas flow through the bypass line 4 and the bypass flow resistance 28, on the one hand, and through the evaporation chamber line 5, on the other hand, and thus it determines the anesthetic concentration that can be preselected by means of the handwheel 24. The carrier gas saturated with the anesthetic 7 from the return line 19 meets the carrier gas, whose composition has not changed, in the bypass line 4 at the junction 27, from which the mLxed gas thus produced reaches the mixed gas outlet 100.

Figure 3:
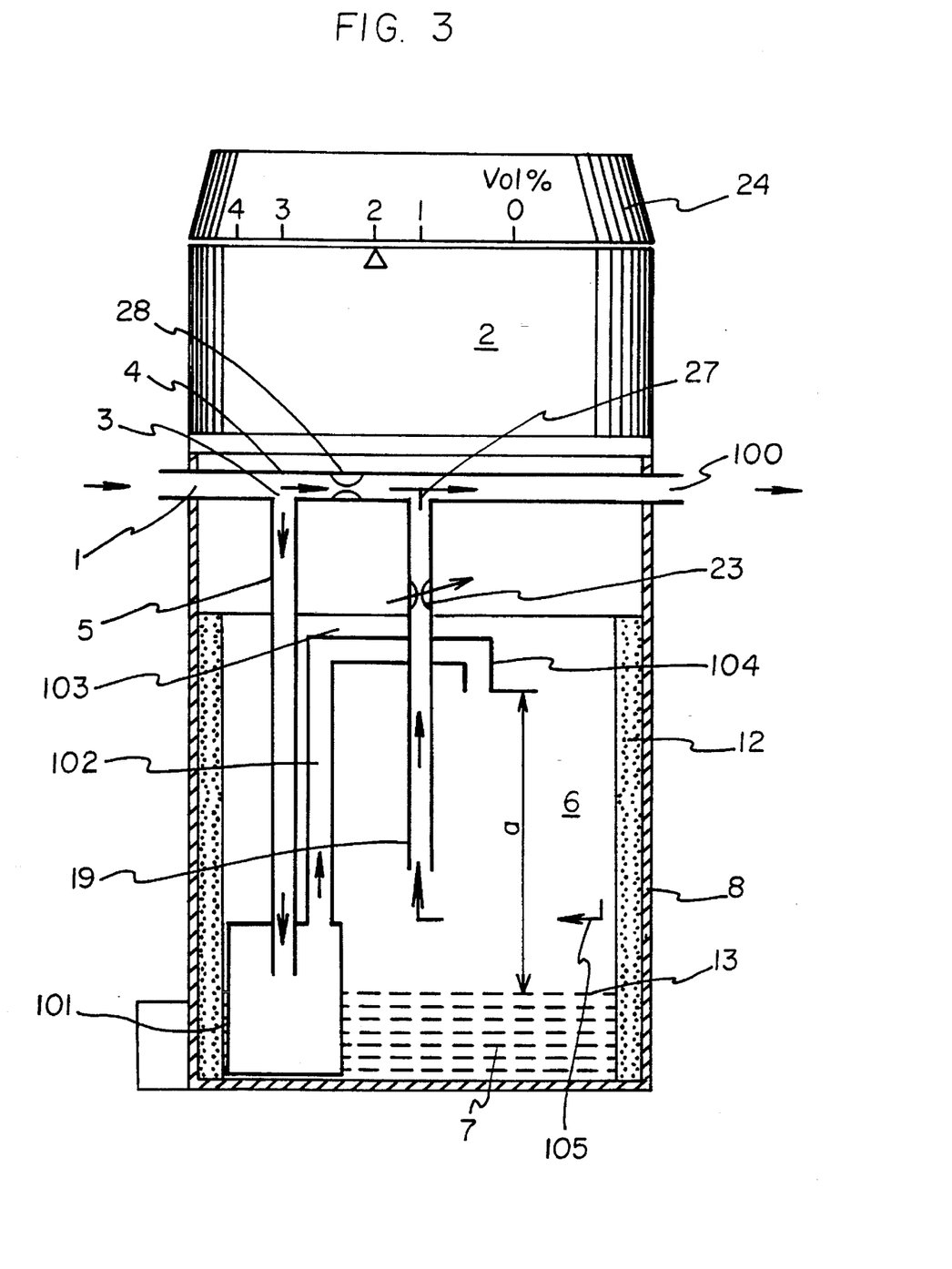
FIG. 3 is a sectional view of an anesthetic evaporator with another embodiment of the intermediate container according to the invention.

The anesthetic evaporator according to FIG. 2 is modified in FIG. 3 such that the channel 102 is led in parallel to the evaporation chamber line over a longer section before it is continued in the channel section 103, which is bent off from it and extends in parallel to the liquid level 13 of the anesthetic 7. The channel section 103 is followed by the end piece 104, which is bent off from it at right angles, and which is located at a distance (a) from the liquid level 13, and whose opening points toward the liquid level 13.

Figure 4:
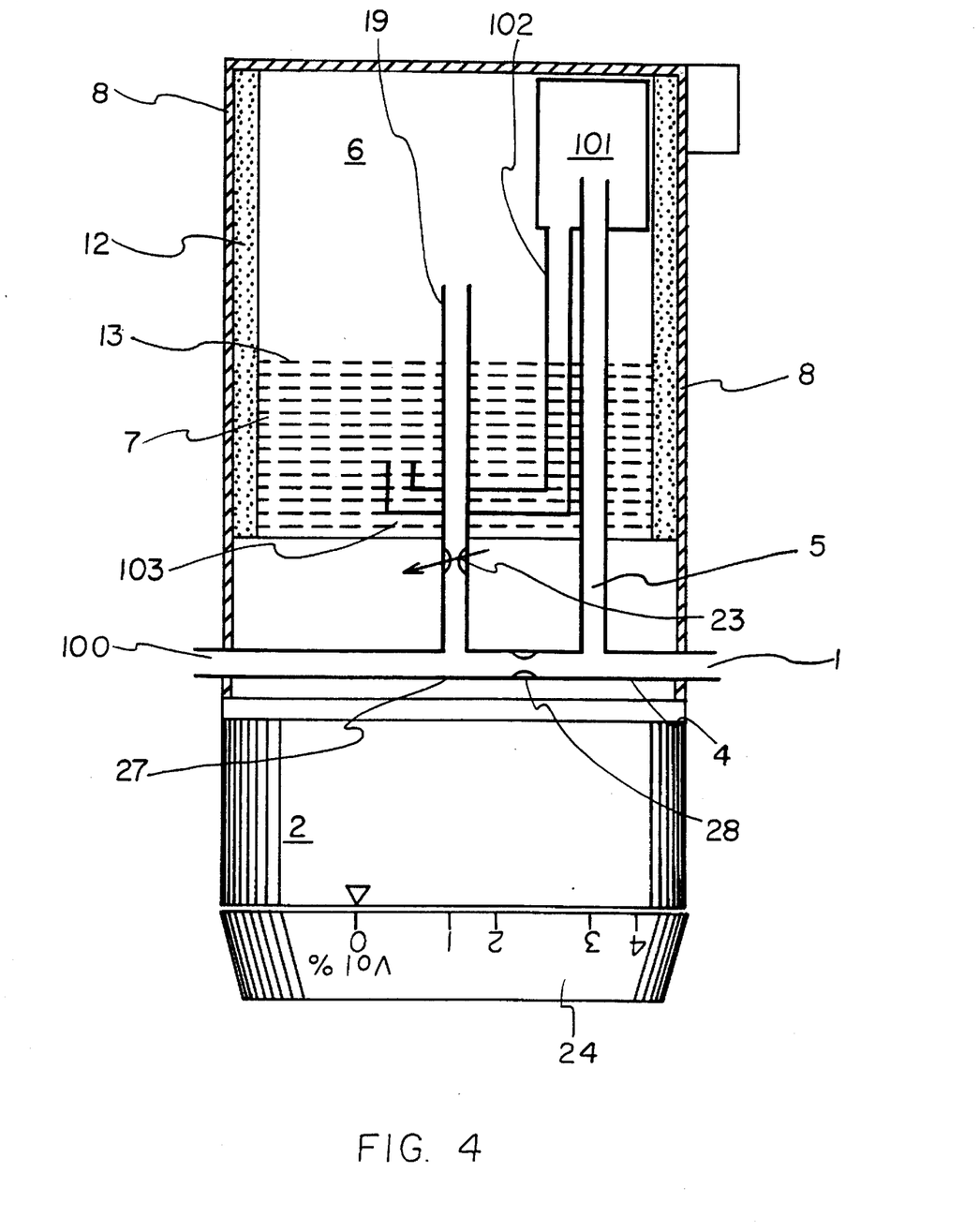
FIG. 4 is a sectional view of the anesthetic evaporator according to FIG. 3 in the upside down position.
Figure 7:
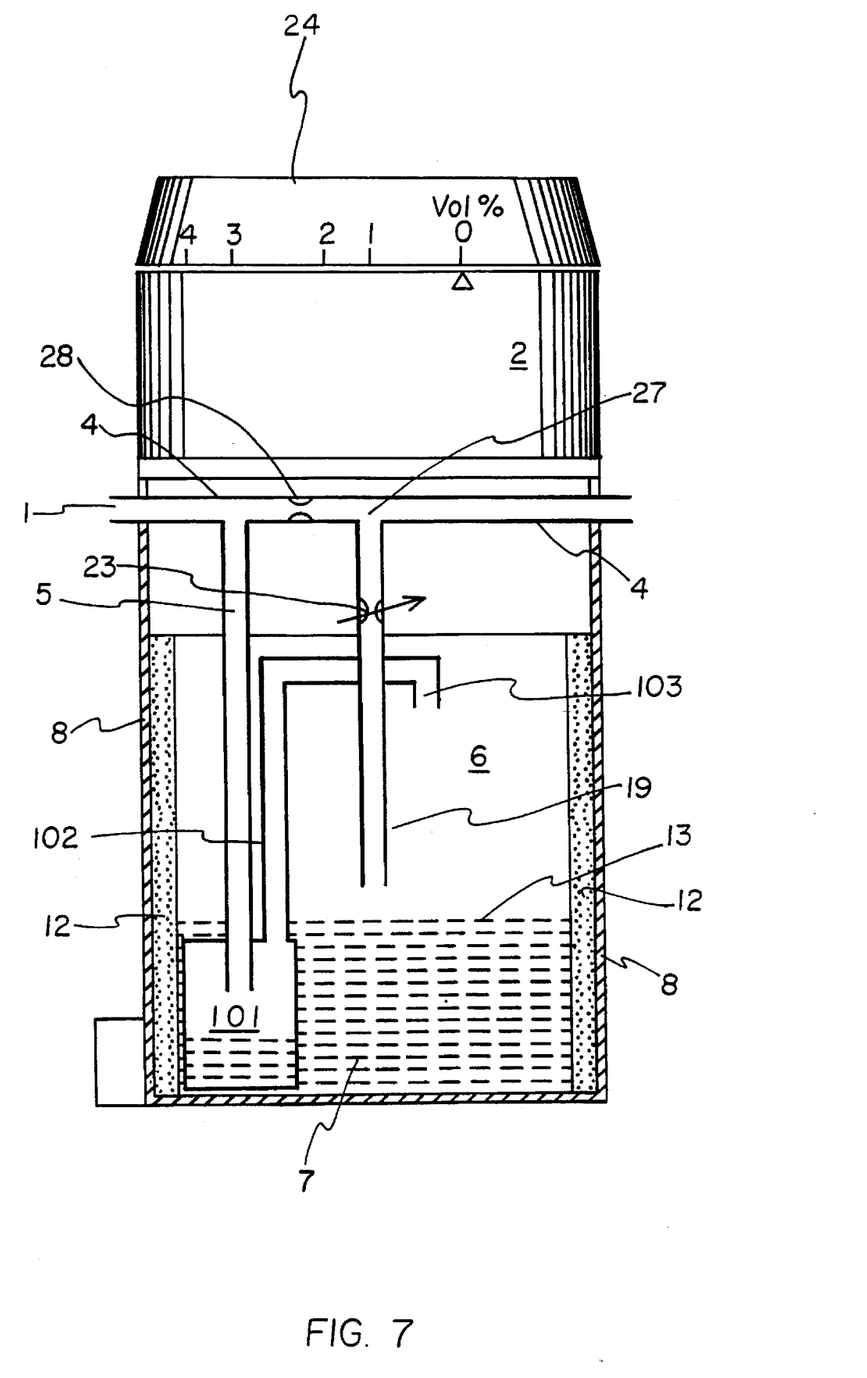
FIG. 7 is a sectional view of the anesthetic evaporator according to FIG. 4, again in the upright position.

FIG. 4 shows an extreme position of the anesthetic evaporator, which is not intended for operation, namely, the position in which the evaporation chamber 6 is located vertically above the handwheel 24 and the flow regulating valves 23, 28. Thus, the anesthetic liquid 7 has flown into the area of the evaporation chamber 6, in which the line section 103 of the channel 102 is located. The channel 102 and the channel section 103 are now filled with the anesthetic 7 to the liquid level 13. When the anesthetic evaporator is subsequently placed upright again into its vertical operating position, the volume of the channel 102 and of the channel section 103, which are filled with the anesthetic 7, are emptied into the intermediate container 101 (see. FIG. 7). The volume of the intermediate container 101 is large enough to be able to take up the surge of the anesthetic 7 from the channel 102 and the channel section 103, without the opening of the evaporation chamber line 5 in the intermediate container 101 being covered. The contents of the intermediate container 101 would not flow into the evaporation chamber line 5 even when the anesthetic evaporator is subsequently again turned upside down, but it would be emptied into the channel 102, so that the amount of the liquid anesthetic 7 entering the intermediate container 101 can never exceed the-amount of the liquid anesthetic 7 taken up for the first time. The amount of the anesthetic 7 that can enter the intermediate container 101 due to an unintended position of the anesthetic evaporator 2 does not consequently exceed the amount which is taken up in the channels 102, 103. Consequently, the entering liquid anesthetic 7 does not accumulate when the anesthetic evaporator is repeatedly in oblique or upside down positions.

Figure 5:
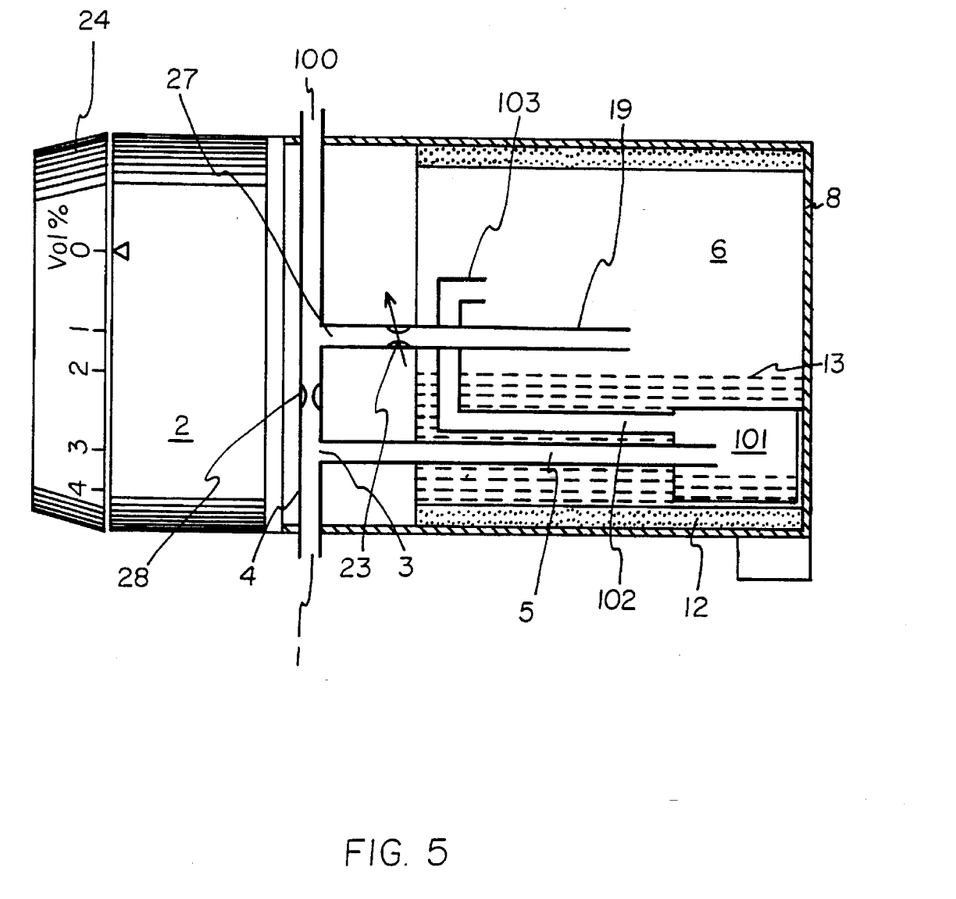
FIG. 5 is a sectional view of the anesthetic evaporator according to FIG. 3 in the lying position.

If the anesthetic evaporator 2 is in a horizontal position FIG. 5, in which the liquid anesthetic 7 rests on a lateral half of the wick 12, the gas-carrying lines, i.e., the evaporation chamber line 5, the channel 102, and the return line 19 still remain unaffected by the anesthetic 7, and even the liquid level of the anesthetic 7 in the intermediate container 101, which has unintentionally penetrated into the intermediate container 101, leaves free the opening of the evaporation chamber line 5 into the intermediate container 101.

Figure 6:
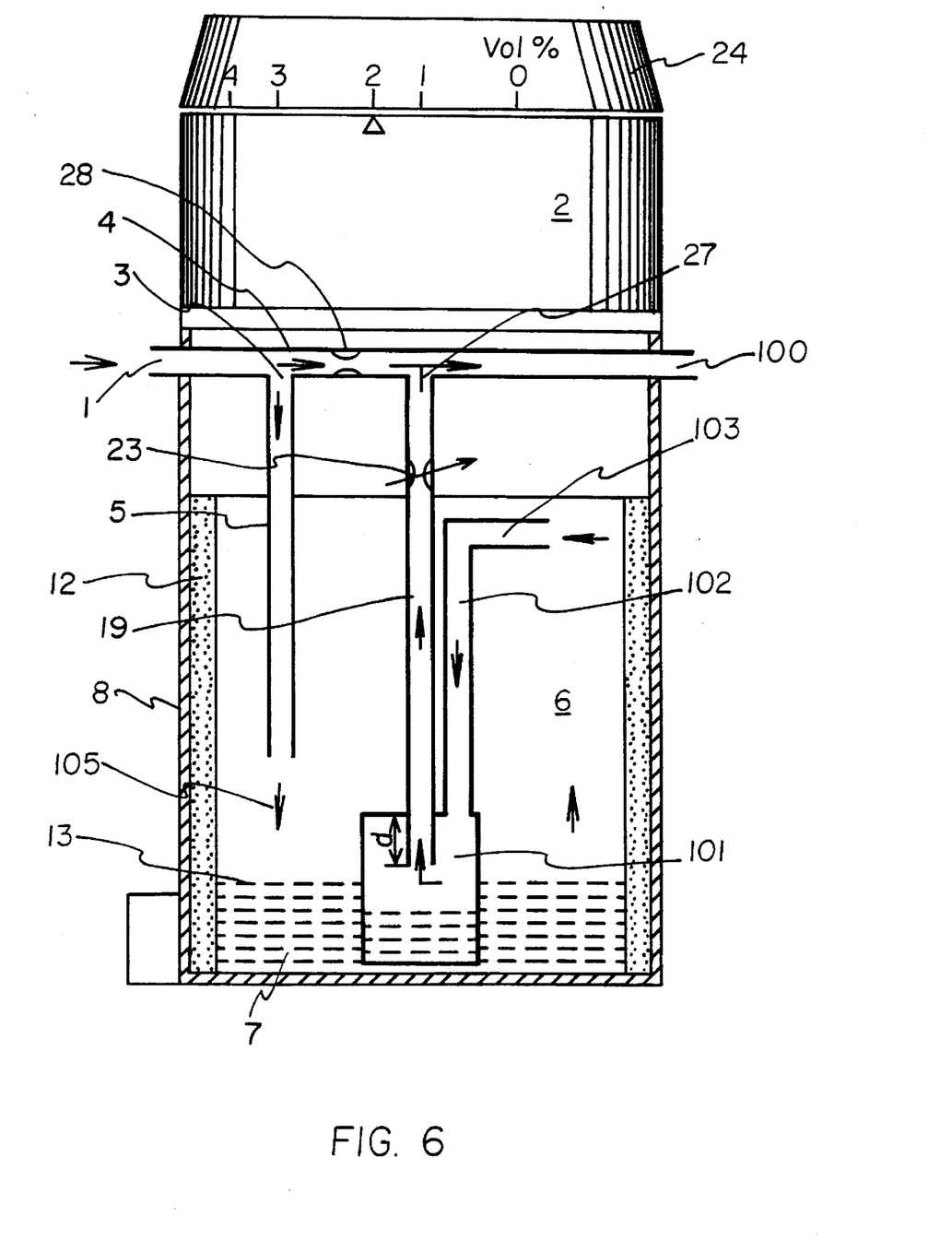
FIG. 6 is a sectional view of an anesthetic evaporator with an intermediate container, connected to the return line.

Finally, FIG. 6 shows another embodiment according to the present invention, in which the return line 19 extends with a depth of penetration (d) into the intermediate container 101, on the bottom of which a residual amount of the anesthetic 7 is located due to a previous unintended position of the anesthetic evaporator 2. The channel 102 communicates with the evaporation chamber 6 such that the flow in the channel 102 is now opposite that shown in FIGS. 2 through 5. The carrier gas, saturated with the anesthetic 7, now penetrates from the evaporation chamber 6 into the line section 103 extending in parallel to the liquid level, and from there into the interior of the intermediate container 101, and it is further sent into the return line 19 via the flow regulating point 23, after which it meets the carrier gas flow in the bypass line 4 at the junction 27 and flows as a mixed gas to the mixed gas outlet 100. As is apparent from FIG. 6, it would be possible to empty the liquid anesthetic 7 present in the intermediate container 101 into the evaporation chamber 6 through the channel 102 by turning the anesthetic evaporator in the direction of the drawing plane inclined to the right. However, it is equally possible, and not detrimental to the proper operation of the anesthetic evaporator, for the liquid anesthetic 7 to remain in the intermediate container 101, to be evaporated by the gas flow taking place in it during the operating time, and to be carried by the gas flow to the flow regulating point 23.

While specific embodiments of the invention have been shown and described in detail to illustrate the application of the principles of the invention, it will be understood that the invention may be embodied otherwise without departing from such principles.

What is claimed is:

1. Anesthetic evaporator, comprising:

a housing defining an evaporation chamber containing a liquid anesthetic, said housing having a gas inlet and a gas outlet, said liquid anesthetic in said evaporation chamber defining a liquid level, said inlete having a point of separation;

a wick device extending into said evaporation chamber, said wick device being impregnated with said liquid anesthetic;

an evaporation chamber line connected to said gas inlet and extending from said point of separation into said evaporation chamber;

a bypass line connected to said gas inlet and extending from said point of separation to said outlet;

a return line connecting said bypass line to said evaporation chamber;

a flow regulating valve arranged in said return line;

adjusting means connected to said flow regulating valve for metering an amount of carrier gas enriched with anesthetic flowing from said evaporation chamber into said bypass line; and an intermediate container forming an independent vessel within said evaporation chamber, at least one of said evaporation chamber line and said return line opening into said intermediate container, said intermediate container having a channel with a channel opening, said channel extending into said evaporation chamber from said intermediate container and communicating with an interior of said evaporation chamber whereby anesthetic which has penetrated into said intermediate chamber can be emptied.

2. Anesthetic evaporator according to claim 1, wherein said intermediate container channel has a line section extending essentially in parallel to said liquid level of anesthetic located in said evaporation chamber when said evaporation chamber is in an essentially upright operating position.

3. Anesthetic evaporator according to claim 2, wherein said channel of said independent vessel is located at a distance from said liquid level.

4. Anesthetic evaporator according to claim 3, wherein said wick is provided along a periphery of said evaporation chamber and said channel opening is positioned substantially centrally with respect to a position of said wick.

5. Anesthetic evaporator.according to claim 2, wherein one of said evaporation chamber line and said return line is continued in said intermediate container with a depth of penetration, said channel being connected to said intermediate container immediately adjacent to one of said evaporation chamber line and said return line.

6. Anesthetic evaporator according to claim 2, wherein said channel is lead at least partially in parallel to one of said evaporation chamber line and said return line.

7. Anesthetic evaporator according to claim 2, wherein said intermediate container has an intermediate container volume and said channel defines a channel volume, wherein said intermediate container volume is approximately three times a volume of said channel volume.

8. Anesthetic evaporator according to claim 4, wherein said depth of penetration of one of said evaporation chamber line and said return line defines on a position for opening within said intermediate container, said channel having a channel volume said intermediate container having a volume which is larger than said channel volume said intermediate container being shaped to define a space free of anesthetic when anesthetic corresponding to said channel volume is present in said intermediate container, said opening being positioned in said space whereby said opening is free of anesthetic in both said upright operating position and any other oblique position of the evaporator chamber inclined relative to a vertical position.

9. Anesthetic evaporator according to claim 2, wherein said intermediate container has an essentially cylindrical shape and includes a top wall.;
    said one of said evaporation chamber line and said return line axially penetrating into top front wall of said intermediate container;
    said channel exiting from said intermediate container, extending flush with said front wall adjacent to one of said evaporation chamber line and said return line.

10. Anesthetic evaporator according to claim 1, wherein said intermediate container has an essentially cylindrical shape and includes a top wall;
    said one of said evaporation chamber line and said return line axially penetrating into said top wall of said intermediate container;
    said channel exiting from said intermediate container, extending flush with said top wall adjacent to one of said evaporation chamber line and said return line.

11. Anesthetic evaporator according to claim 3, wherein said channel includes an end piece bent at approximately right angles from said line section, said end piece extending in parallel to said liquid level of said anesthetic located in said evaporation chamber when said evaporation chamber is in an essentially upright operating position.

12. Anesthetic evaporator according to claim 1, wherein said end piece is bent off pointing away from said liquid level of said anesthetic located in said evaporation chamber when said evaporation chamber is in an essentially upright. operating position.

13. Anesthetic evaporator according to claim 11, wherein said end piece is bent off pointing toward a liquid level of said anesthetic located in said evaporation chamber when said evaporation chamber is in an essentially upright operating position.

14. An anesthetic evaporator according to claim 2, wherein said intermediate container has an intermediate container volume and said channel defines a channel volume, said intermediate container volume being greater than said channel volume.

15. An anesthetic evaporator according to claim 1, wherein said intermediate container includes a top wall, said channel starting from said top wall and extending a distance away from said liquid level of anesthetic located in said evaporation chamber when said evaporation chamber is in an essentially upright operating position.

16. Anesthetic evaporator, comprising:
    a housing defining an evaporation chamber containing a liquid anesthetic, said housing having a gas inlet and a gas outlet, said liquid anesthetic in said evaporation chamber defining a liquid level, said inlet having a point of separation;
    a wick device extending into said evaporation chamber, said wick device being impregnated with said liquid anesthetic;
    an evaporation chamber line connected to said gas inlet and extending from said point of separation into said evaporation chamber;
    a bypass line connected to said gas inlet and extending from said point of separation to said gas outlet;
    a return line connecting said bypass line to said evaporation chamber;
    a flow regulating valve arranged in said return line;

adjusting means connected to said flow regulating valve for metering an amount of carrier gas enriched with anesthetic flowing from said evaporation chamber into said bypass line; and an intermediate container forming an independent vessel within said evaporation chamber, at least one of said evaporation chamber line and said return line opening into said intermediate container, said intermediate container having a channel with a channel opening, said intermediate container including a top wall, said channel starting from said top wall and extending from said top wall in parallel to said evaporation chamber line, extending into said evaporation chamber from said intermediate container and communicating with an interior of said evaporation chamber whereby anesthetic which has penetrated into said intermediate chamber can be emptied.

* * * * *